(12) United States Patent
Kralovec et al.

(10) Patent No.: US 11,466,231 B2
(45) Date of Patent: Oct. 11, 2022

(54) PROCESS FOR THE PRODUCTION OF DIGLYCERIDES

(71) Applicant: DSM IP Assets B.V., Heerlen (NL)

(72) Inventors: Jaroslav A. Kralovec, Halifax (CA); Paul Frederick Mugford, Halifax (CA); Alfred Rolle, Dartmouth (CA)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 16/972,153

(22) PCT Filed: Jun. 4, 2019

(86) PCT No.: PCT/EP2019/064545
§ 371 (c)(1),
(2) Date: Dec. 4, 2020

(87) PCT Pub. No.: WO2019/234057
PCT Pub. Date: Dec. 12, 2019

(65) Prior Publication Data
US 2021/0238499 A1 Aug. 5, 2021

Related U.S. Application Data

(60) Provisional application No. 62/680,702, filed on Jun. 5, 2018.

(51) Int. Cl.
*C11C 3/02* (2006.01)
*C07C 67/02* (2006.01)
*C07C 69/28* (2006.01)
*C11C 3/06* (2006.01)

(52) U.S. Cl.
CPC .............. *C11C 3/02* (2013.01); *C07C 67/02* (2013.01); *C07C 69/28* (2013.01); *C11C 3/06* (2013.01)

(58) Field of Classification Search
CPC ..... C11C 3/02; C11C 3/06; C11C 1/04; C07C 67/02; C07C 69/28
See application file for complete search history.

(56) References Cited

U.S. PATENT DOCUMENTS

| | | | |
|---|---|---|---|
| 6,261,812 B1 * | 7/2001 | Yamada | C11C 1/04 435/134 |
| 8,227,010 B2 * | 7/2012 | Kase | C12P 7/6418 426/601 |
| 8,410,181 B2 | 4/2013 | Deckelbaum et al. | |
| 8,536,232 B2 | 9/2013 | Deckelbaum et al. | |
| 8,633,253 B2 | 1/2014 | Deckelbaum et al. | |
| 9,084,801 B2 | 7/2015 | Deckelbaum et al. | |
| 9,144,562 B2 | 9/2015 | Deckelbaum et al. | |
| 9,675,572 B2 | 6/2017 | Lewis | |
| 10,070,643 B2 | 9/2018 | Deckelbaum et al. | |
| 11,076,593 B2 | 8/2021 | Deckelbaum et al. | |
| 2005/0214434 A1 | 9/2005 | Yoon et al. | |
| 2005/0214914 A1 * | 9/2005 | Sato | C12P 7/62 435/134 |
| 2009/0324574 A1 * | 12/2009 | Mathur | C12N 9/14 514/1.1 |

FOREIGN PATENT DOCUMENTS

| | | | |
|---|---|---|---|
| EP | 0191217 A1 | 8/1986 | |
| EP | 1135991 A2 * | 9/2001 | ............... A23D 9/00 |
| WO | 2021211796 A1 | 10/2021 | |

OTHER PUBLICATIONS

Liu, M., et al., Fast production of diacylglycerol in a solvent free system via lipase catalyzed esterification using a bubble column reactor, J. Am. Oil. Chem. Soc., vol. 93, No. 5, pp. 637-648 (Year: 2016).*

Xu, D., et al., Enzymatic synthesis of diacylglycerols enriched with conjugated linoleic acid by a novel lipase from Malassezia globosa, J. Am. Oil chem. Soc., vol. 89, No. 7, pp. 1259-1266 (Year: 2012).*

Zheng, P., et al., Production of diacylglycerol-mixture of regioisomers with high purity by two-step enzymatic reactions combined with molecular distillation, J. Am. Oil Chem. Soc., vol. 91, No. 2, pp. 251-259 (Year: 2013).*

International Search Report of International Patent Application No. PCT/EP2019/064545 dated Dec. 12, 2019, 5 pages.

Liu Manman et al. "Fast Production of Diacylglycerol in a Solvent Free System via Lipase Catalyzed Esterification Using a Bubble Column Reactor," Journal of the American Oil Chemists' Society (JAOCS), vol. 93, No. 5, dated Feb. 23, 2016, pp. 637-648, XP035947575, ISSN: 0003-021X, DOI: 10.1007/s11746-016-2804-y.

Pingyu Zheng et al. "Production of Diacylglycerol-Mixture of Regioisomers with High Purity by Two-Step Enxymatic Reactions Combined with Molecular Distillation," Journal of the American Oil Chemists' Society (JAOCS), vol. 91, No. 2, dated Oct. 17, 2013, pp. 251-259, XP055614567, ISSN: 0003-021X, DOI: 10.1007/s11746-013-2365-2.

Da Xu et al. "Enzymatic Synthesis of Dioleylglycerols Enriched with Conjugated Linoleic Acid by a Novel Lipase From," Journal of the American Oil Chemists' Society (JAOCS), vol. 89, No. 7, dated Feb. 1, 2012, pp. 1259-1266, XP035083294, ISSN: 1558-9331, DOI: 10.1007/S11746-012-2018-X.

Pastor E et al. "Synthesis of Mono- And Dioleylglycerols Using an Immobilized Lipase," Applied Biochemistry and Biotechnology, vol. 50, No. 3, dated Jan. 1, 1995, pp. 251-263, XP008058633, ISSN: 0273-2289, DOI: 10.1007/BF02788096.

(Continued)

*Primary Examiner* — Yate' K Cutliff
(74) *Attorney, Agent, or Firm* — Morgan, Lewis & Bockius LLP

(57) ABSTRACT

A method for producing diglycerides is provided. The method includes combining (i) an oil comprising at least one polyunsaturated fatty acid in the form of ethyl esters, free fatty acids, and/or combinations thereof, (ii) lipase, and (iii) glycerol in water to produce diglycerides with a high level of purity. Highly pure diglycerides obtained according to the method are also provided.

16 Claims, No Drawings

Specification includes a Sequence Listing.

(56) References Cited

OTHER PUBLICATIONS

Phuah Eng-Tong et al. "Review on the Current State of Diacylglycerol Production Using Enzymatic Approach," Food and Bioprocess Technology, An International Journal, vol. 8, No. 6, dated Mar. 26, 2015, pp. 1169-1186, XP035498670, ISSN: 1935-5130, DOI: 10.1007/S11947-015-1505-0.

* cited by examiner

SEQUENCE LISTING

```
<160> NUMBER OF SEQ ID NOS: 1

<210> SEQ ID NO 1
<211> LENGTH: 315
<212> TYPE: PRT
<213> ORGANISM: Candida antarctica

<400> SEQUENCE: 1

Leu Pro Ser Gly Ser Asp Pro Ala Phe Ser Gln Pro Lys Ser Val Leu
1               5                   10                  15
```

-continued

```
Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
 50                      55                  60

Trp Ile Ser Pro Pro Pro Phe Met Leu Asn Asp Thr Gln Val Asn Thr
 65                  70                  75                  80

Glu Tyr Met Val Asn Ala Ile Thr Ala Leu Tyr Ala Gly Ser Gly Asn
                 85                  90                  95

Asn Lys Leu Pro Val Leu Thr Trp Ser Gln Gly Gly Leu Val Ala Gln
             100                 105                 110

Trp Gly Leu Thr Phe Phe Pro Ser Ile Arg Ser Lys Val Asp Arg Leu
             115                 120                 125

Met Ala Phe Ala Pro Asp Tyr Lys Gly Thr Val Leu Ala Gly Pro Leu
 130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
             165                 170                 175

Val Pro Thr Asn Leu Tyr Ser Ala Thr Asp Glu Ile Val Gln Pro Gln
             180                 185                 190

Val Ser Asn Ser Pro Leu Asp Ser Ser Tyr Leu Phe Asn Gly Lys Asn
             195                 200                 205

Val Gln Ala Gln Ala Val Cys Gly Pro Leu Phe Val Ile Asp His Ala
             210                 215                 220

Gly Ser Leu Thr Ser Gln Phe Ser Tyr Val Val Gly Arg Ser Ala Arg
225                 230                 235                 240

Ser Thr Thr Gly Gln Ala Arg Ser Ala Asp Tyr Gly Ile Thr Asp Cys
             245                 250                 255

Asn Pro Leu Pro Ala Asn Asp Leu Thr Pro Glu Gln Lys Val Ala Ala
             260                 265                 270

Ala Ala Leu Leu Ala Pro Ala Ala Ala Ile Val Ala Gly Pro Lys
             275                 280                 285

Gln Asn Cys Glu Pro Asp Leu Met Pro Tyr Ala Arg Pro Phe Ala Val
             290                 295                 300

Gly Lys Arg Thr Cys Ser Gly Ile Val Thr Pro
305                 310                 315
```

PROCESS FOR THE PRODUCTION OF DIGLYCERIDES

CROSS-REFERENCE TO RELATED APPLICATION

This application is a National Phase of International Application No. PCT/EP2019/064545 filed Jun. 4, 2019, which claims the benefit of the filing date of United States Provisional Patent Application No. 62/680,702 filed Jun. 5, 2018, the disclosure of which is hereby incorporated herein by reference in its entirety.

SEQUENCE LISTING

The instant application contains a Sequence Listing which has been submitted in ASCII format via EFS-Web and is hereby incorporated by reference in its entirety. The ASCII copy, created on Apr. 29, 2022, is 3,177 bytes in size and is named, "DT-003_122198-5003_SequenceListing_ST25".

BACKGROUND

The present disclosure relates to processes for producing diglycerides. The process includes combining marine oil ethyl esters, free fatty acids, and combinations thereof, lipase, and alcohol in water to produce diglycerides with a high level of purity.

The beneficial effects of the long-chain polyunsaturated fatty acids (PUFAs) that are characteristic of marine lipids, especially cis-5,8,11,14,17-eicosapentaenoic acid (EPA) and cis-4,7,10,13,16,19-docosahexaenoic acid (DHA) on lowering serum triglycerides are now well established. These compounds are also known for other cardioprotective benefits and other biological effects. Among the most frequently mentioned benefits are those related to the prevention of and the treatment of inflammation, neurodegenerative diseases, and cognitive development abnormalities. The public is becoming increasingly aware of the health benefits of fish oil and DHA and EPA concentrates, as it is evidenced from global sales of polyunsaturated fatty acids (PUFAs).

Several methods of producing PUFA concentrates from marine oils are known, for example, selective lipase hydrolysis, PUFA complexation using urea (or more sophisticated molecular guest-host frameworks involving metric control), and a physical removal of unwanted components by fractionation. U.S. Publication No. 2004/0236128 describes the separation of EPA from DHA by precipitating EPA magnesium salt.

Diacylglycerols (DAGs) are widely used in a variety of applications such as additives for improving plasticity of oils and fats, as well as edible oils in the food industry, and as a base material for the production of cosmetics and drugs. Recently, foods focused on the beneficial physiological activities of diacylglycerols have attracted attention.

However, there are few examples of processes for producing PUFA-containing diglycerides.

U.S. Pat. No. 6,361,980 describes a process for preparing diacylglycerol, which comprises use of an enzyme-packed tower that includes an immobilized lipase preparation, carrying out an esterification reaction between: (1) an acyl group donor selected from the group consisting of a fatty acid, a lower alcohol ester thereof, and a mixture thereof; and (2) an acyl group acceptor selected from the group consisting of glycerol, a monoacylglycerol, and a mixture thereof; to obtain a reaction fluid from said enzyme-packed tower; reducing the water content or lower alcohol content in said reaction fluid; and subsequent to said reducing, recirculating the reaction fluid to said enzyme-packed tower, wherein a residence time of said reaction fluid in said enzyme-packed tower is 120 seconds or less; to obtain a diacylglycerol, wherein said reducing comprises dehydrating or de-alcoholizing said reaction fluid is by feeding said reaction fluid though a spray nozzle, in a dehydration process. However, this process is costly, as it requires the use of expensive purified fatty acids as raw material, immobilized lipase, and a specialized packed-enzyme tower reactor. This process produces diglycerides of moderate purity (88.6-91.7%; DG Purity=DG/(DG+TG), their purity being reduced by the difficult to separate triglycerides also formed in this method.

JP 2004208539 describes a process for producing PUFA-containing diglycerides in which a PUFA or its lower alkyl ester and glycerin are reacted in the presence of immobilized partial glyceride lipase while removing water produced during the reaction outside the reaction system. However, the method requires monitoring the acid value of the reaction and the purity of the diglycerides obtained is low. The percent % DG purity was from 66-85%; DG Purity =DG/(DG+TG) (triglycerides were also formed)

JP2004222594 describes a two-step process for producing PUFA-containing fats and oils, wherein glycerol is reacted in the presence of water and lipase in the presence of water and lipase to perform a glycerolysis reaction, and the resulting PUFA-containing partial glycerides and fatty acids or lower alkyl esters thereof are reacted in the presence of immobilized partial glyceride lipase. However, the method requires two separate steps and purity of the diglycerides obtained is low. % DG purity=57% to 68% (triglycerides also formed?)

CN101736044 describes a method to continuously enzymatically synthesize n-3 PUFA glyceride comprising mixing n-3 PUFA (EPA, DHA) and glycerin into a reaction liquid, and pumping the reaction liquid into the apparatus through a constant flow pump into an enzyme reaction column with immobilized lipase. The esterification rate of the n-3 PUFA glyceride product prepared by the continuous synthesis method is 30-50%, the monoester content is 20-30%, the diester content is 50-70%, and the triester content is 10-20%. Thus, amount and purity of the diacylglycerol obtained by this method is low.

CN101818176 describes a method for transforming fatty acid ethyl ester into glyceride, which comprises the following steps of: mixing the fatty acid ethyl ester and glycerol in a material tank; making the material pass through a glycerol separator by using a pump to separate free glycerin; then putting the material in a reactor in which immobilized lipase is filled; and making the material pass through a packed tower to remove ethanol; making the material finally flow back to the material tank for performing 6 to 300 hours circular reaction; then carrying out molecular distillation on the reaction product to remove the unconverted reactant so as to obtain glyceride products. Similar to the above method, a mixture of monoacylglycerol, diacylglycerol, and triacylglycerol is obtained, with the concentration of diacylglycerol ranging from approximately 20-30%.

US20070148745 describes producing a diacylglycerol, which comprises reacting triacylglycerol with water and an enzyme, such as an immobilized lipase, to obtain a mixture comprising diacylglycerol, monoacylglycerol and free fatty acid; removing water content in the mixture by way of dehydration; and separating monoacylglycerol, free fatty acid and residual triacylglycerol by at least one separation method to obtain a high-purity diacylglycerol. Thus, this method actually results in obtaining a mixture of glycerides as described above and requires additional steps to separate the diacylglycerols from the monoacylglycerols, triacylglycerols and free fatty acids. In particular, the reaction of triacylglycerol with water and immobilized lipase resulted in a composition comprising about 41-44% diacylglycerol. After separation, a composition comprising about 88-90% diacylglycerol was obtained.

Thus, there remains a need to provide improved processes for the production of highly pure diglycerides.

The solution to this technical problem is provided by the embodiments characterized below.

BRIEF SUMMARY

The present application provides methods for producing diglycerides. In particular, the method of the invention includes combining (i) an oil comprising at least one polyunsaturated fatty acid in the form of ethyl esters, free fatty acids, or combinations thereof, (ii) lipase, and (iii) glycerol in water to produce diglycerides with a high level of purity.

In some embodiments, the lipase is lipase B derived from *Candida antarctica*.

In some embodiments, water is added back into the reaction at a sufficient rate to replace the water evaporated under vacuum, and this water level is maintained for about the first 4-12 hours of the reaction.

In some embodiments, the reaction is performed under reduced pressure. In some embodiments, the reaction is performed at about 20 mTorr.

After the reaction is completed, the reaction mixture may be washed one or more times with, for example, water, brine, or any combination thereof.

The reaction mixture may be dried, for example, under vacuum until all or essentially all residual water is removed from the reaction mixture.

Any remaining ethyl esters, monoacylglycerols, and/or free fatty acids may be separated from the diacylglycerols by, for example, distillation.

It will be understood that the steps of the method of the invention may be performed in any order. In some embodiments, one or more steps of the method of the invention may be performed more than once. In a preferred embodiment, the steps of the method of the invention are performed in the order listed above.

Also provided is a diglyceride obtained according to the method of the invention.

Further provided is the use of the diglyceride obtained according to the method of the invention in a food product, a dietary supplement, a pharmaceutical product, or a cosmetic product.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Thus, for example, reference to "a compound" includes mixtures of two or more such compounds, reference to "an unsaturated fatty acid" includes mixtures of two or more such unsaturated fatty acids, reference to "the matrix" includes mixtures of two or more such matrices, and the like.

Unless defined otherwise, all technical and scientific terms used herein have the same meaning as commonly understood to one of ordinary skill in the art to which this disclosure belongs.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application, data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Reference will now be made in detail to specific aspects of the disclosed materials, compounds, compositions, articles, and methods, examples of which are illustrated in the accompanying Examples and Figures.

Disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a compound is disclosed and a number of modifications that can be made to a number of components or residues of the compound are discussed, each and every combination and permutation that are possible are specifically contemplated unless specifically indicated to the contrary. Thus, if a class of components or residues A, B, and C are disclosed as well as a class of components or residues D, E, and F and an example of a combination compound A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

As used herein, the terms "diacylglycerol", "diglyceride", and "diester" are used interchangeably to refer to two fatty acids attached to a glycerol backbone. Similarly, the terms "monoacylglycerol" and "monoglyceride" are used interchangeably to refer to one fatty acid attached to a glycerol backbone and the terms "triacylglycerol", "triglyceride", and "trimester" are used interchangeably to refer to three fatty acids attached to a glycerol backbone.

Enzymes

The enzymes useful herein are any naturally occurring or synthetic enzymes that can be used to esterify a carboxylic acid or transesterify an ester. The term "esterify" is defined herein as the conversion of a carboxylic acid to the corresponding ester by reacting the carboxylic acid with an alcohol to produce the ester (e.g., RCOOH+ $R^1OH \rightarrow RCOOR^1+H_2O$). The term "transesterify" is defined herein as the conversion of one ester to another by reacting the ester with an alcohol to produce a different ester (e.g., $RCOOR^1+R^2OH \rightarrow RCOOR^2+R^1OH$). The term "interesterify" is defined herein as the switching of ester moieties between two or more separate, independent esters. Interesterification between two esters is depicted in scheme 1A, where the $R^2$ and $R^4$ groups are switched in the starting materials (i.e., $R^1COOR^2$ and $R^3COOR^4$). Scheme 1B depicts the interesterification between a carboxylic acid ($R^1COOH$) and an ester ($R^3COOR^4$), which produces a new carboxylic acid and ester. The term "intraesterify" is defined herein as the switching of ester moieties within the same molecule. Intraesterification is depicted in scheme 1C, where the $R^2$ and $R^3$ groups are switched in the triester. Scheme 1D depicts the intraesterification between a carboxylic acid group and an ester within the same molecule, where hydrogen of the carboxylic acid switches with $R^3$ of the ester group.

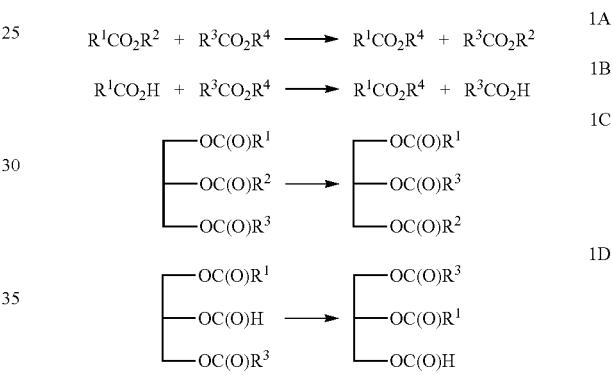

Scheme 1

Suitable enzymes can be derived from a microorganism. Examples of microorganisms that can produce enzymes useful herein include, but are not limited to, *Burkholderia* sp., *Candida antarctica* B, *Candida rugosa*, *Candida cylindracea*, *Pseudomonas* sp., *Candida antarctica* A, *Porcine pancreas*, *Humicola* sp., *Humicola lanuginose*, *Mucor miehei*, *Rhizopus javan.*, *Pseudomonas fluor*, *Pseudomonas cepacia*, *Candida cylindrcae*, *Aspergillus niger*, *Rhizopus oryzae*, *Mucor jaanicus*, *Mucor javanicus*, *Rhizopus* sp., *Rhizopus japonicus*, *Rhizomucor miehi*, *Rhizopus niveus*, or penicillium camembertii (also *Rhizopus delemar*, *Pseudonomas aeruginosa*).

In one example, the enzyme is produced from *Candida antarctica*. NOVOZYME™ CALB L is a lipase (lipase B) from *Candida antarctica* produced by submerged fermentation of a genetically modified *Aspergillus oryzae* microorganism. NOVOZYME™ CALB L is a highly versatile catalyst with activity towards a great variety of different substrates. The enzyme is used in particular as a powerful enantioselective catalyst in the synthesis of optically active alcohols, amines, and carboxylic acids. *Candida antarctica* lipase B is known to effectively convert ethyl esters or free fatty acids to triglycerides. This enzyme is a protein with 317 amino acid residues and molecular weight of 33,008 Daltons. The amino acids are assembled into 14 α-helixes and 9 β-sheets. The amino acid sequence and secondary structure of *Candida antarctica* lipase B are provided in SEQ ID NO: 1.

```
LPSGSDPAFSQPKSVLDAGLTCQGASPSSVSKPILLVPGTGTTGPQSFDSN

WIPLSTQLGYTPCWISPPPFMLNDTQVNTEYMVNAITALYAGSGNNKLPVL

TWSQGGLVAQWGLTFFPSIRSKVDRLMAFAPDYKGTVLAGPLDALAVSAPS

VWQQTTGSALTTALRNAGGLTQIVPTNLYSATDEIVQPQVSNSPLDSSYLF

NGKNVQAQAVCGPLFVIDHAGSLTSQFSYVVGRSARSTTGQARSADYGITD

CNPLPANDLTPEQKVAAAALLAPAAAAIVAGPKQNCEPDLMPYARPFAVGK

RTCSGIVTP
```

It is also contemplated that derivatives of enzymes produced from microorganisms can be used in the methods described herein. It is understood that the structure of many enzymes, as disclosed herein, are known and can be found, for example, at Genbank, and are herein incorporated by reference.

As all microbial lipases, CALB belongs to α/β hydrolases, the fold of which comprises of eight-stranded β-sheets sandwiched between two layers of amphiphilic α-helices. The mechanism of ester hydrolysis of these enzymes generally involves binding to the ester substrate, formation of the first tetrahedral intermediate by nucleophilic attack of the catalytic serine with the oxyanion stabilized by two or three H-bonds, the so-called oxyanion hole. The ester bond is cleaved and the acylated enzyme is hydrolyzed in the final step. The nucleophilic attack by the catalytic serine is mediated by the catalytic histidine and aspartic or glutamic acid residue. In certain examples, the longest fatty acid chain that completely binds inside the binding pocket of CALB is C13; thus, the scisille fatty acid binding site of this enzyme is relatively short (13.5 Å). The binding site of CALB is relatively short and has a small hydrophobic area located at the wall of the binding funnel. Structure of CALB has been published in the Protein Data Bank (The Protein Data Bank: a computer-based archival file for macromolecular structures. Bernstein et al., J. Mol. Biol. 112:525-542, 1977). It is also understood that their conserved catalytic cores, which are understood in the art and are herein disclosed, can define the disclosed enzymes.

Sequence Similarities

It is understood that as discussed herein the use of the terms "homology" and "identity" mean the same thing as similarity. Thus, for example, if the use of the word homology is used between two non-natural sequences, it is understood that this is not necessarily indicating an evolutionary relationship between these two sequences but rather is looking at the similarity or relatedness between their sequences. Many of the methods for determining homology between two evolutionarily related molecules are routinely applied to any two or more nucleic acids or proteins for the purpose of measuring sequence similarity, regardless of whether they are evolutionarily related or not. In general, it is understood that one way to define any known variants and derivatives or those that might arise of the disclosed genes and proteins herein, such as SEQ ID NO: 1, is through defining the variants and derivatives in terms of homology to specific known sequences. This identity of particular sequences disclosed herein is also discussed elsewhere herein. In general, variants of genes and proteins herein disclosed typically have at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence.

Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman, Adv. Appl. Math. 2:482, 1981, by the homology alignment algorithm of Needleman and Wunsch, J. Mol. Biol. 48:443, 1970, by the search for similarity method of Pearson and Lipman, Proc. Natl. Acad. Sci. U.S.A. 85:2444, 1988, by computerized implementations of these algorithms (GAP, BESTFIT, PASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, Science 244:48-52, 1989, Jaeger et al., Proc. Natl. Acad. Sci. U.S.A. 86:7706-7710, 1989, Jaeger et al., Methods Enzymol. 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Hybridization/Selective Hybridization

It is also understood that the enzymes disclosed herein, such as SEQ ID NO: 1, can be classified by the ability of the nucleic acids encoding them to hybridize with other nucleic acids. The term "hybridization" typically means a sequence driven interaction between at least two nucleic acid molecules, such as a primer or a probe and a gene. The phrase "sequence driven interaction" means an interaction that occurs between two nucleotides or nucleotide analogs or nucleotide derivatives in a nucleotide specific manner. For example, G interacting with C or A interacting with T are sequence driven interactions. Typically, sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some examples selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12 to about 25° C. below the Tm (the melting temperature at which half of the molecules dissociate from their hybridization partners), followed by washing at a combination of temperature and salt concentration chosen so that the washing temperature is about 5° C. to about 20° C. below the Tm. The temperature and salt conditions are readily determined empirically in preliminary experiments in which samples of reference DNA immobilized on filters are hybridized to a labeled nucleic acid of interest and then washed under conditions of different stringencies.

Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. *Methods Enzymol.* 1987:154:367, 1987, which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in, for example, 10, or 100, or 1000-fold excess. This type of assay can be performed at under conditions where both the limiting and non-limiting primer are, for example, 10-fold, or 100-fold, or 1000-fold below their $k_d$, or where only one of the nucleic acid molecules is 10-fold, or 100-fold, or 1000-fold, or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some examples selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation; for example, if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example, if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Peptides

As discussed herein there are numerous variants and strain derivatives of the disclosed enzymes, such as SEQ ID NO: 1 are known and herein contemplated. Enzymes can be made from proteins or peptides. Protein variants and derivatives are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion.

Deletions are characterized by the removal of one or more amino acid residues from the protein sequence. Typically, no more than about from 2 to 6 residues are deleted at any one site within the protein molecule. These variants ordinarily are prepared by site-specific mutagenesis of nucleotides in the DNA encoding the protein, thereby producing DNA encoding the variant, and thereafter expressing the DNA in recombinant cell culture.

Techniques for making substitution mutations at predetermined sites in DNA having a known sequence are well known, for example M13 primer mutagenesis and PCR mutagenesis. Amino acid substitutions are typically of single residues but can occur at a number of different locations at once; insertions usually will be on the order of from about 1 to 10 amino acid residues; and deletions will range from about 1 to 30 residues.

Deletions or insertions preferably are made in adjacent pairs, i.e., a deletion of 2 residues or insertion of 2 residues. Substitutions, deletions, insertions, or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables A and B and are referred to as conservative substitutions.

TABLE A

Amino Acid Abbreviations

| Amino Acid | Abbreviations |
| --- | --- |
| Alanine | Ala (A) |
| Alloisoleucine | AIle |
| Arginine | Arg (R) |
| Asparagine | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |
| Isoleucine | Ile (I) |
| Leucine | Leu (L) |
| Lysine | Lys (K) |
| Methionine | Met (M) |
| Phenylalanine | Phe (F) |
| Proline | Pro (P) |
| Pyroglutamic Acid | Glu |
| Serine | Ser (S) |
| Threonine | Thr (T) |
| Tyrosine | Tyr (Y) |
| Tryptophan | Trp (W) |
| Valine | Val (V) |

TABLE B

Amino Acid Substitutions
Original Residue Exemplary Conservative
Substitutions, others are known in the art.

Ala ↔ ser
Arg ↔ lys or gln
Asn ↔ gln or his
Asp ↔ glu
Cys ↔ ser
Gln ↔ asn or lys
Glu ↔ asp
Gly ↔ pro
His ↔ asn or gln
Ile ↔ leu or val
Leu ↔ ile or val
Lys ↔ arg or gln;
Met ↔ Leu or ile
Phe ↔ leu or tyr
Ser ↔ thr
Thr ↔ ser
Trp ↔ tyr
Tyr ↔ trp or phe
Val ↔ ile or leu Substantial changes in function or immunological identity are made by selecting substitutions that are less conservative than those in Table B, i.e., selecting residues that differ more significantly in their effect on maintaining: (a) the structure of the polypeptide backbone in the area of the substitution, for example as a sheet or helical conformation; (b) the charge or hydrophobicity of the molecule at the target site; or (c) the bulk of the side chain. The substitutions that are generally expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or pro line is substituted for (or by) any other residue; (c) a residue having an electropositive side chain, e.g., lysyl, arginyl, or histidyl is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, are accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of pro line and lysine, phosphorylation of hydroxyl groups of seryl or threonyl residues, methylation of the amino groups of lysine, arginine, and histidine side chains (T. E. Creighton, Proteins: Structure and Molecular Properties, W. H. Freeman & Co., San Francis.co pp 79-86 (1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of a lipase. Specifically disclosed are variants of these and other proteins herein disclosed which have at least about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman, *Adv. Appl. Math.* 2:482, 1981, by the homology alignment algorithm of Needleman and Wunsch, *J. Mal. Biol.* 48:443, 1970, by the search for similarity method of Pearson and Lipman, *Proc. Natl. Acad. Sci. U.S.A.* 85:2444, 1988, by computerized implementations of these algorithms (GAP, BESTFIT, PASTA, and TFASTA in the Wisconsin Genetics Software Package, Genetics Computer Group, 575 Science Dr., Madison, Wis.), or by inspection.

The same types of homology can be obtained for nucleic acids by, for example, the algorithms disclosed in Zuker, Science 244:48-52, 1989, Jaeger et al., *Proc. Natl. Acad. Sci. U.S.A.* 86:7706-7710, 1989, Jaeger et al., *Methods Enzymol* 183:28.1-306, 1989, which are herein incorporated by reference for at least for their material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is also understood that while no amino acid sequence indicates what particular DNA sequence encodes that protein within an organism, where particular variants of a disclosed protein are disclosed herein, the known nucleic acid sequence that encodes that protein in the particular strain from which that protein arises is also known and herein disclosed and described.

It is understood that there are numerous amino acid and peptide analogs, which can be incorporated into the disclosed compositions. For example, there are numerous D amino acids or amino acids that have a different functional substituent then the amino acids shown in Table A and Table B. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons to insert the analog amino acid into a peptide chain in a site-specific way (Thorson et al., *Meth. Mol. Biol.* 77:43-73, 1991; Zoller, *Curr. Opinion Biotechnol.* 3:348-354, 1992; Ibba, *Biotechnol. Gen. Eng. Rev.* 13:197-216, 1995; Cahill et al., *TIBS* 14(10):400-403, 1989; Benner, *TIB Tech* 12:158-163, 1994; Ibba and Hennecke, *Bio/technology* 12:678-682, 1994, all of which are herein incorporated by reference at least for their material related to amino acid analogs).

Molecules can be produced that resemble peptides, but which are not connected via a natural peptide linkage. For example, linkages for amino acids or amino acid analogs can include, but are not limited to, CH2NH—, —CH2S—, —CH2-CH2—, —CH=CH(cis and trans), —COCH2—, —CH(OH)CH2—, and —CHH2SO— (These and others can be found in Spatola, in Chemistry and Biochemistry of Amino Acids, Peptides, and Proteins, B. Weinstein, eds., Marcel Dekker, New York, p. 267, 1983; Spatola, Vega Data (March 1983), Vol. 1, Issue 3, Peptide Backbone Modifications (general review); Morley, *Trends Pharm. Sci.* 463-468, 1980; Hudson et al., *Int. J Pept. Prot. Res.* 14:177-185., 1979 (—CH2NH—, CH2CH2-); Spatola et al., *Life Sci.* 38:1243-1249, 1986 (—CH2-S); Hann, *J Chem. Soc Perkin Trans.*1307-314, 1982 (—CH=CH—, cis and trans}; Almquist et al., *J Med. Chem.* 23:1392-1398, 1980 (—COCH2—); Jennings-White et al., *Tetrahedron Lett.* 23:2533, 1982 (—COCH2-); Szelke et al., European App. No. EP 45665 CA (1982): 97:39405 (1982) (—CH(OH) CH2-); Holladay et al., *Tetrahedron. Lett.* 24:4401-4404, 1983 (—C(OH)CH2-); and Hruby, *Life Sci.* 31:189-199, 1982 (—CH2-S—); each of which is incorporated herein by reference. A particularly preferred non-peptide linkage is —CH2NH—. It is understood that peptide analogs can have more than one atom between the bond atoms, such as (1-alanine, -y-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D-amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch, Ann. Rev. Biochem. 61: 387, 1992, which is incorporated herein by reference).

Use of Enzymes

Described herein are methods for esterifying a carboxylic acid that comprise reacting the carboxylic acid with an alcohol in the presence of any of the enzymes described herein. In a further aspect, described herein are methods for transesterifying an ester that comprise reacting the ester with an alcohol in the presence of any of the enzymes described herein. In a still further aspect, described herein are methods for interesterifying two or more different carboxylic acids or esters thereof that comprise reacting the carboxylic acids or esters with each other in the presence of any of the enzymes described herein. In yet a still further aspect, described herein are methods for intraesterifying a compound comprising at least two ester groups or a compound comprising at least one carboxylic acid group and one ester group, that comprise contacting the compound with any of the enzymes described herein. A schematic of the transesterification of an ethyl ester (EE) to a triglyceride or an esterification of a free fatty acid (FFA) to a triglyceride is shown below.

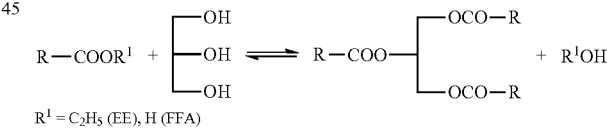

$R^1 = C_2H_5$ (EE), H (FFA)

Although the esterification of any carboxylic acid, the transesterification of any ester, the interesterification of two or more different carboxylic acids/esters, or the intraesterification of a compound is contemplated using the methods described herein, in many examples, a fatty acid or the ester thereof can be used in any of the methods. In certain examples, the ester of the fatty acid is a $C_1$-$C_6$ branched or straight chain alkyl ester such as, for example, methyl, ethyl, propyl, butyl, pentyl, and the like.

In other specific examples, a fatty acid or the ester thereof can be used in the methods described herein. By "fatty acid" is meant a carboxylic acid with at least 10 carbon atoms. In one aspect, the fatty acid or the ester thereof can comprise at least 10, at least 12, at least 14, at least 16, at least 18, or at least 20 carbon atoms. In some specific examples, the fatty acid or the ester thereof can contain 10, 11, 12, 13., 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. In other examples, the fatty acid or the ester thereof can comprise a mixture of fatty acids or the esters thereof having a range of carbon atoms. For example, the fatty acid or the ester thereof can comprise from about 10 to about 40, from about 12 to about 38, from about 14 to about 36, from about 16 to about 34, from about 18 to about 32, or from about 20 to 30 carbon atoms.

The fatty acids or esters thereof can be saturated, unsaturated, or a mixture of saturated and unsaturated fatty acids. By "saturated" is meant that the molecule or residue contains no carbon-carbon double or triple bounds. By "unsaturated" is meant that the molecule or residue contains at least one carbon-carbon double or triple bond.

In one specific example, the fatty acids or the esters thereof can be derived from marine oils, such as fish oil, prior to esterification. Such oils typically contain mixtures of saturated and unsaturated fatty, acids, but can be processed to result in a particular mixture of fatty acids (e.g., containing all saturated, all unsaturated, mixtures of both, or mixtures with fatty acids of a certain chain length or range of chain lengths). Any fish oil can be used in the disclosed compounds arid methods. Examples of suitable fish oils include, but are not limited to, Atlantic fish oil, Pacific fish oil, Mediterranean fish oil, light pressed fish oil, alkaline treated :fish oil, heat treated fish oil, light and heavy brown fish oil, bonito oil, pilchard oil, tuna oil, sea bass oil, halibut oil, spearfish oil, barracuda oil, cod oil, menhaden oil, sardine oil, anchovy oil, capelin oil, Atlantic cod oil, Atlantic herring oil, Atlantic mackerel oil, Atlantic menhaden oil, salmonid oil, and shark oil, including mixtures and combinations thereof. Non-alkaline treated fish oil is also suitable. Other marine oils suitable for use herein include, but are not limited to, squid oil, cuttle fish oil, octopus oil, krill oil, seal oil, whale oil, and the like, including mixtures and combinations thereof. Any marine oil and combination of marine oil can be used in the disclosed compositions and in the disclosed methods to prepare them. Further oils include, microbial oil, algal oil (e.g., oil from a dinoflagellate such as *Crypthecodinium cohnii* or e.g., oil from *Thraustochytrium, Schizochytrium,* or a mixture thereof), fungal oil (e.g., oil from *Mortierella alpina*), and/or plant oil, including mixtures and combinations thereof.

Examples of specific saturated fatty acids or esters thereof useful herein include, but are not limited to, capric acid (C10), lauric acid (C12), myristic acid (C14), palmitic acid (C16), margaric acid (C17), stearic acid (C18), arachidic acid (C20), behenic acid (C22), lignoceric acid (C24), cerotic acid (C26), montanic acid (C28), and melissic acid (C30), including branched and substituted derivatives thereof.

The unsaturated fatty acids or esters thereof suitable for the methods disclosed herein can comprise at least one unsaturated bond (i.e., a carbon-carbon double or triple bond). In one example, the unsaturated fatty acid or ester thereof can comprise at least 2, at least 3, at least 4, at least 5, at least 6, at least 7, at least 8, at least 9, or at least 10 carbon-carbon double bonds, triple bonds, or any combination thereof. In another example, the unsaturated fatty acid or ester thereof can comprise 1, 2, 3, 4, 5, 6, 7, 8, 9, or 10 unsaturated bonds, where any of the stated values can form an upper or lower endpoint when appropriate.

In one example, the unsaturated fatty acids or esters thereof can comprise one carbon-carbon double bond (i.e., a monoene acid or residue). Examples of unsaturated fatty acids or esters thereof that are suitable for the methods disclosed herein include, but are not limited to, those in the following Table 1.

TABLE 1

Examples of monoene acids

| Total Number of Carbon Atoms in the Fatty Acid Chains | Carbon number where double bond begins. ("c" denotes a cis double bond; "t" denotes a trans double bond) |
|---|---|
| 10 | 4c |
| 12 | 4c |
| 14 | 4c and 9c |
| 16 | 3t, 4c, 5t, 6c, 6t, 9c (palmitooleic), and 11c |
| 18 | 3t, 5c, 5t, 6c (petroselinic), 6t, 9c (oleic), 10c, 11c (cis-vaccenic), 11t (vaccenic), and 13c |
| 20 | 5c, 9c (gadolenic), 11c, 13c, and 15c |
| 22 | 5c, 11c (cetoleic), 13c (erucic), and 15c |
| 24 | 15c (selacholeic, nervonic) |
| 26 | 9c, and 17c (ximenic) |
| 28 | 9c, 19c (lumequic) |
| 30 | 21c |

In other examples, the unsaturated fatty acids or esters thereof can comprise at least two unsaturated bonds (e.g., polyene acids or residues). In some examples, the unsaturated fatty acids or esters thereof can comprise at least one pair of methylene interrupted unsaturated bonds. By "methylene interrupted unsaturated bond" is meant that one carbon-carbon double or triple bond is separated from another carbon-carbon double or triple bond by at least one methylene group (i.e., $CH_2$). Specific examples of unsaturated fatty acids or esters thereof that contain at least one pair of methylene interrupted unsaturated bonds include, but are not limited to, the n-1 family derived from 9, 12, 15-16:3; n-2 family derived from 9, 12, 15-17:3, 15:3, 17:3, 17:4, 20:4; n-3 family derived from 9, 12, 15-18:3, 15:2, 15:3, 15:4, 16:3, 16:4, 18:3 (α-linolenic), 18:4, 18:5, 20:2, 20:3, 20:4; 20:5 (EPA), 21:5, 22:3, 22:5 (DPA), 22:6 (DHA), 24:3, 24:4, 24:5, 24:6, 26:5, 26:6, 28:7, 30:5; n-4 family derived from 9, 12-16:2, 16:2, 16:3, 18:2, 18:3; n-5 family derived from 9, 12-17:2, 15:2, 17:2, 17:3, 19:2, 19:4, 20:3, 20:4, 21:4, 21:5; n-6 family derived from 9, 12-18:2, 15:2, 16:2, 18:2 (linoleic acid), 18:3 (γ-linolenic acid); 20:2, 20:3, 20:4 (arachidonic acid), 22:2, 22:3, 22:4 (adrenic acid), 22:5, 24:2, 24:4, 25:2, 26:2, 30:4; n-7 family derived from 9-16:1, 15:2, 16:2, 17:2, 18.:2, 19:2; n-8 family derived from 9-17:1, 15:2, 16:2, 17:2, 18:2, 19:2; n-9 family derived from 9-18:1, 17:2, 18:2, 20:2, 20:3, 22:3, 22:4; n-11 family 19:2, and the n-12 family 20:2.

The numbering scheme begins at the terminal end of the fatty acid where, for example, the terminal $CH_3$ group is designated position 1. In this sense, the n-3 family would be an omega-3 fatty acid, as described herein. The next number identifies the total number of carbon atoms in the fatty acid. The third number, which is after the colon, designates the total number of double bonds in the fatty add. So, for example, in the n-1 family, 16:3, refers to a 16 carbon long fatty acid with 3 double bonds, each separated by a methylene, wherein the first double bond begins at position 1, i.e., the terminal end of the fatty acid. In another example, in the n-6 family, 18:3 refers to an 18 carbon long fatty acid with 3 methylene-separated double bonds beginning at position 6, i.e., the sixth carbon from the terminal end of the fatty acid, and so forth.

Some other examples are fatty acids or esters thereof that contain at least one pair of unsaturated bonds interrupted by more than one methylene group. Suitable examples of these acids and esters include, but are not limited to, those in the following Table 2:

TABLE 2

Examples of Polyene Acids

| Total number of carbon atoms in the fatty acid chain | Carbon number where double bond begins. ("c" denotes a cis double bond; "t" denotes a trans double bond) |
|---|---|
| 18 | 5, 9 |
|  | 5, 11 |
|  | 2t, 9, 12 |
|  | 3t, 9, 12 |
|  | 5t, 9, 12 |
|  | 5, 9, 12 |
|  | 5, 11, 14 |
|  | 3t, 9, 12, 15 |
|  | 5, 9, 12, 15 |
| 20 | 5, 11 |
|  | 5, 13 |
|  | 7, 11 |
|  | 7, 13 |
|  | 5, 11, 14 |
|  | 7, 11, 14 |
|  | 5, 11, 14, 17 |
| 22 | 5, 11 |
|  | 5, 13 |
|  | 7, 13 |
|  | 7, 15 |
|  | 7, 17 |
|  | 9, 13 |
|  | 9, 15 |

Still other examples of unsaturated fatty acids or esters thereof that are suitable for use in the methods disclosed herein are those that contain at least one conjugated unsaturated bond. By "conjugated unsaturated bond" is meant that at least one pair of carbon-carbon double and/or triple bonds are bonded together, without a methylene ($CH_2$) group between them (e.g., —CH=CH—CH=CH—). Specific examples of unsaturated fatty acids or esters thereof that contain conjugated unsaturated bonds include, but are not limited to, those in the following Table 3.

TABLE 3

Examples of Conjugated Polyene Acids

| Total number of carbon atoms in the fatty chain | Carbon number where double bond begins. ("c" denotes a cis double bond; "t" denotes a trans double bond) |
|---|---|
| 10 | 2t, 4t, 6c |
|  | 2c, 4t, 6t |
|  | 3t, 5t, 7c |
|  | 3c, 5t, 7t |
| 12 | 3, 5, 7, 9, 11 |
| 14 | 3, 5, 7, 9, 11 |
| 18 | 10t, 12t |
|  | 8c, 10t, 12c (jacaric) |
|  | 5t, 10t, 12c (calendic) |
|  | 5t, 10t, 12t |
|  | 9t, 11t, 13c (catalpic) |
|  | 9c, 11t, 13c (α-eleostearic) |
|  | 9c, 11t, 13c (punicic) |
|  | 9t, 11t, 13t (β-eleostearic) |
|  | 9c, 11t, 13c, 15c (α-parinaric) |
|  | 9t, 11t, 13t, 15t (β-parinaric) |

Omega-3 fatty acids and esters thereof are also useful in the methods described herein. Omega-3 fatty acids are unsaturated fatty acids that are particularly useful in the compounds and methods disclosed herein. Omega-3 fatty acids not only exhibit proven effects on lowering serum triglyceride levels, but they have strong connection to diabetes. For instance, docosahexaenoic acid (DHA) also has a strong insulin permeability enhancement effect, and it is viewed as a potential absorption enhancer for intestinal delivery of insulin (Onuki et al., *Int. J. Pharm.* 198:147-56, 2000). DHA intake prevents certain biochemical processes that originate from insulin deficiency (Ovide-Bordeaux and Grynberg, *Am. J. Physiol. Regul. Integr. Comp. Physiol.* 286:R519-27, 2003) and both DHA and BPA (eicosapentaenoic acid) significantly increase fasting insulin levels (Mori et al., *Am. J. Clin. Nutr.* 71: 1085-94, 2000).

An omega-3 fatty acid is an unsaturated fatty acid that contains as its terminus $CH_3$—$CH_2$—CH=CH—. Specific examples of omega-3 fatty acids and esters thereof that are suitable for use herein include, but are not limited to, linolenic acid (18:3ω3), octadecatetraenoic acid (18:4ω3), eicosapentaenoic acid (20:5ω3) (EPA), docosahexaenoic acid (22:6ω3) (DHA), docosapentaenoic acid (22:6ω3) (DPA), derivatives thereof and mixtures thereof.

In still other examples, unsaturated fatty acids and esters thereof can be derived from a compound comprising the following formula:

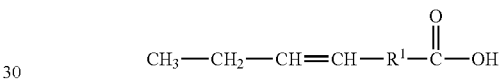

wherein $R^1$ is a $C_3$-$C_{40}$ alkyl or alkenyl group comprising at least one double bond. The term "alkane" or "alkyl" as used herein is a saturated hydrocarbon group. The term "alkene" or "alkenyl" as used herein is a hydrocarbon group of at least 2 carbon atoms with a structural formula containing at least one carbon-carbon double bond. Asymmetric structures such as (AB)C=C(CD) are intended to include both the E and Z isomers (cis and trans). This may be presumed in structural formulae herein wherein an asymmetric alkene is present, or it may be explicitly indicated by the bond symbol C=C. In a further example, $R^1$ can be a $C_5$-$C_{38}$, $C_6$-$C_{36}$, $C_8$-$C_{34}$, $C_{10}$-$C_{32}$, $C_{12}$-$C_{30}$, $C_{14}$-$C_{28}$, $C_{16}$-$C_{26}$, or $C_{18}$-$C_{24}$ alkenyl group. In yet another example, the alkenyl group of $R^1$ can have from 2 to 6, from 3 to 6, from 4 to 6, or from 5 to 6 double bonds. Still further, the alkenyl group of $R^1$ can have from 1, 2, 3, 4, 5, or 6 double bonds, where any of the stated values can form an upper or lower endpoint when appropriate.

Some specific examples of unsaturated fatty acids and esters thereof that can be used in the methods disclosed herein include, but are not limited to, linoleic acid, linolenic acid, γ-linolenic acid, arachidonic acid, mead acid, stearidonic acid, α-eleostearic acid, eleostearic acid, pinolenic acid, docosadienic acid, docosatetraenoic acid, docosapentaenoic acid, docosahexaenoic acid, octadecadienoic acid, octadecatrienoic acid, eicosatetraenoic acid, eicosapentaenoic, or any combination thereof. In one aspect, the unsaturated fatty acid ester can be derived from linolenic acid (18:3ω3), octadecatetraenoic acid (18:4ω3), eicosapentaenoic acid (20:5ω3) (EPA), eicosatetraenoic acid (20:4ω3), henicosapentaenoic acid (21:5ω3), docosahexaenoic acid (22:6ω3) (DHA), docosapentaenoic acid (22:5ω3) (DPA), including derivatives and mixtures thereof.

Additional examples of suitable unsaturated fatty acid and esters thereof that are suitable in the methods include, but are not limited to, allenic and acetylenic acids, such as C14:

2, 4, 5; C18: 5, 6 (laballenic); 5, 6, 16 (lamenallenic); C18: 6a (tarinic); 9a; 9a, 11t (ximenynic); 9a, 11a; 9a, 11a, 13c (bolekic); 9a, 11a, 13a, 15e, 8a, 10t (pyrulic) 9c, 12a (crepenynic); 9c, 12a, 14c (dehydrocrepenynic acid); 6a, 9c, 12c; 6a, 9c, 12c, 15c, 8a, 11c, 14c and corresponding Δ7e derivatives, 8-OH derivatives, and Δ17e, 8-OH derivatives.

Branched-chain acids and esters thereof, particularly iso-acids and anteiso acids, polymethyl branched acids, phytol based acids (e.g., phytanic, pristanic), furanoid acids are also suitable fatty acids, for use in the methods disclosed herein.

Still further, suitable fatty acids and esters thereof include, but are not limited to, cyclic acids, such as cyclopropane fatty acids, cyclopropene acids (e.g., lactobacillic), sterulic, malvalic, sterculynic, 2-hydroxysterculic, aleprolic, alepramic, aleprestic, aleprylic alepric, hydnocarpic, chaulmoogric hormelic, manaoic, garlic, oncobic, cyclopentenyl acids, and cyclohexylalkanoic acids.

Hydroxy acids and esters thereof, particularly butolic, ricinoleic, isoricinoleic, densipolic, lesquerolic, and auriolic are also suitable fatty acids that upon esterification can be used in the methods disclosed herein.

Epoxy acids and esters, particularly epoxidated C18:1 and C18:2, and furanoid acids and esters are further examples that can be used in the disclosed methods.

In some embodiments, the oil comprising at least one polyunsaturated fatty acid in the form of ethyl esters, free fatty acids, and/or combinations thereof is docosahexaenoic acid (DHA), eicosopentaenoic acid (EPA), or combinations thereof.

In some embodiments, the amount of DHA (mg/g of oil) in the oil comprising at least one polyunsaturated fatty acid in the form of ethyl esters, free fatty acids, and/or combinations thereof is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

In some embodiments, the amount of EPA (mg/g of oil) in the oil comprising at least one polyunsaturated fatty acid in the form of ethyl esters, free fatty acids, and/or combinations thereof is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

In some embodiments, the amount of DHA (mg/g of oil) and EPA (mg/g of oil) in the oil comprising at least one polyunsaturated fatty acid in the form of ethyl esters, free fatty acids, and/or combinations thereof is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

In some embodiments, the amount of DHA (mg/g of oil) in the oil in the diglyceride produced is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

In some embodiments, the amount of EPA (mg/g of oil) in the oil in the diglyceride produced is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

In some embodiments, the amount of DHA (mg/g of oil) and EPA (mg/g of oil) in the oil in the diglyceride produced is from about 100 mg to about 950 mg, about 100 mg to about 800 mg, about 100 mg to about 700 mg, about 100 mg to about 600 mg, about 100 mg to about 500 mg, about 100 mg to about 400 mg, about 100 mg to about 300 mg, about 100 mg to about 200 mg, or about 0 to about 100 mg.

The alcohol used in any of the methods disclosed herein can be any alcohol. In one example, the alcohol is a polyol, which is defined as a compound having two or more hydroxyl groups. Examples of polyols useful herein include, but are not limited to, pentaerythritol, dipentaerythritol, tripentaerythritol, tetrapentaerythritol, tris(hydroxymethyl)ethane, or tris(hydroxymethyl)propane. In other examples, the alcohol is a sugar such as, for example, a glucosamine, a methyl glucoside, or other sugars such as, for example, sucrose. In another example, the polyol is glycerol.

The amount of carboxylic acid/ester and alcohol used will vary depending upon the acid, ester, and alcohol selected. In one example, a stoichiometric amount of carboxylic acid or ester relative to number of hydroxyl groups present on the alcohol can be used. For example, if the alcohol is a diol, then two molar equivalents of carboxylic acid or ester can be esterified or transesterified, respectively, with one molar equivalent of diol. An excess of alcohol can be used to achieve maximum esterification or transesterification as well as decrease the overall reaction time. In one aspect, when the alcohol is glycerol, the molar ratio of carboxylic acid or ester to alcohol is from 0.1:1 to 6:1, from 1:1 to 3:1, from 1.5:1 to 2.5:1, or from 2:1 to 3:1.

The amount of the enzyme can also vary as well. In one example, the enzyme is from 0.1% to 20% by weight of total weight of carboxylic acid/ester and alcohol. In other examples, the enzyme is 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16; 17, 18, 19, 20% by weight of the total reaction, where any value can form an endpoint of a range.

The amount of water can also vary. In one example, the ratio of carboxylic acid/ester to water is from 1:1 to 15:1, from 1:1 to 12:1, from 1:1 to 10:1, from 1:1 to 9:1, from 1:1 to 8:1, from 1:1 to 7:1, from 1:1 to 6:1, from 1:1 to 5:1, from 1:1 to 4:1, from 1:1 to 3:1, or from 1:1 to 2:1. In another example, the ratio of carboxylic acid/ester to water is from 1:1 to 15:1, from 2:1 to 15:1, from 3:1 to 15:1, from 4:1 to 15:1, from 5:1 to 15:1, from 6:1 to 15:1, from 7:1 to 15:1, from 8:1 to 15:1, from 9:1 to 15:1, from 10:1 to 15:1, or from 12:1 to 15:1.

The carboxylic acid/ester, the alcohol, the enzyme, and the water can be admixed with one another in any order. Depending upon the selection of the carboxylic acid/ester and the alcohol, it can be desirable to conduct the esterification or transesterification while the reaction mixture is stirred. For example, a solution of ester and alcohol can be added to one another under stirring followed by the addition of the enzyme.

In one aspect, water is added during the reaction to replace water lost due to evaporation, etc. Water may be added continuously or occasionally throughout the duration of the reaction. For example, water may be added when the volume of the reaction falls below a predefined threshold. Water may be added throughout the entire reaction or during part of the reaction. For example, water may be added during the beginning of the reaction and discontinued later in the reaction; e.g., water may be added during the first quarter; the first third; or the first half of the reaction.

In certain aspects, the esterification, transesterification, and interesterification/intraesterification reactions can take place at an elevated temperature. The precise elevated temperature can depend on the particular carboxylic acid or ester being used, the particular alcohol being used, the amount or concentration of the reagents, preference, and the like. Suitable temperatures at which the esterification and transesterification reactions can occur include, but are not limited to, from about 30° C. to about 90° C., from about 60° C. to about 90° C., from about 80° C. to about 90° C., or about 85° C. In another example, the esterification temperature can be from about 50° C. to about 70° C., or about 60° C. By varying the temperature, it is possible to reduce reaction times depending upon the concentration of starting materials. Thus, reaction times can vary from 2 hours to 72 hours, 2 hours to 48 hours, 2 hours to 24 hours, 6 hours to 48 hours, 6 hours to 36 hours, 8 hours to 24 hours, 8 hours to 16 hours, or 8 hours to 12 hours.

The esterification, transesterification, and interesterification/intraesterification reactions may be performed at reduced pressure. For example, the esterification, transesterification, and interesterification/intraesterification reactions may be performed at a pressure from about 1 mTorr to about 200 mTorr, from about 5 mTorr to about 100 mTorr, from about 10 mTorr to about 50 mTorr, from about 15 mTorr to about 30 mTorr, or at about 20 mTorr.

In other examples, the method involves esterifying eicosapentaenoic acid 20:5ω3 (EPA), docosahexaenoic acid 22:6ω3 (DHA), docosapentaenoic acid 22:5ω3 (DPA), or any mixture thereof with glycerol, wherein the acid and the alcohol are present in a molar ratio of from about 1:1 to about 3:1, wherein the reaction is stirred in the presence of the enzyme and water at a temperature of from about 30° C. to about 90° C. at reduced pressure for about 2 hours to about 24 hours, wherein the enzyme comprises an enzyme derived from *Candida antarctica*.

In another aspect, the method involves transesterifying an ethyl ester of eicosapentaenoic acid 20:5ω3 (EPA), docosahexaenoic acid 22:6ω3 (DHA), docosapentaenoic acid 22:5ω3 (DPA), or any mixture thereof with glycerol, wherein the ester and the alcohol are present in a molar ratio of from about 1:1 to about 3:1, wherein the reaction is stirred in the presence of the enzyme and water at a temperature of from about 30° C. to about 90° C. at reduced pressure for about 2 hours to about 24 hours, wherein the enzyme comprises an enzyme derived from *Candida antarctica*.

The methods described herein are efficient with respect to producing primarily diacylglycerols with very little triacylglycerols formed. Since any remaining ethyl esters, monoacylglycerols and free fatty acids can be easily removed (e.g., by distillation), highly pure diacylglycerols can be obtained using this method. In addition, the amount of diacylglycerol as a percentage of the total product is from about 80% to about 100%; optionally from about 90% to about 100%; optionally from about 95% to about 100%; optionally from about 96% to about 100%; optionally from about 96.5% to about 100%; optionally from about 97% to about 100%; optionally from about 97.5% to about 100%; optionally from about 98% to about 100%; optionally from about 98.5% to about 100%; optionally from about 99% to about 100%; optionally from about 99.5% to about 100%.

The separation methods for use in separating monoacylglycerols, free fatty acids and residual triacylglycerols from diacylglycerols include, but are not limited to deodorization, short-path distillation, steam distillation, molecular distillation, adsorption chromatography, or any combination thereof. The separation methods may be conducted batchwise, continuous, and semi-continuous.

The resulting product may by further processed. The refined product may also be stabilized, for example, by the addition of a-tocopherol.

The following examples are offered to illustrate, but not to limit, the claimed invention.

EXAMPLES

Example 1

Preparation of eicosapentaenoic acid (EPA)/docosahexaenoic acid (DHA)-diacylglycerides (DAG)

The preparation of diacylglycerol from highly concentrated ethyl esters was facilitated by a one-pot hydrolysis followed by re-esterification in the presence of lipase B from *Candida antarctica* (CAL-B) under reduced pressure.

To a 1 L flask fitted with concentrator condenser, a mixture of omega-3 concentrated ethyl ester (EPA: 439 mg/g; DHA: 405 mg/g; 300 g), glycerol (60 g), and CAL-B (5000 LU/g, 1.9 g) in water (75.0 g) was added and stirred under vacuum (20 mTorr) at 60° C. for 8-12 hours. For the first 4-6 hours, water was replaced at a rate of 15 mL/hr.

Upon completion, the reaction mixture was washed with water (45° C., 300 mL) followed by a brine wash (45° C., 300 mL) and a final water wash (45° C., 300 mL). The mixture was dried under high vacuum (100 mTorr) at a temperature of approximately 65° C. overnight (12-15 hours). The unreacted ethyl ester, the generated monoacylglycerides, and other low boiling components were removed by short path distillation (200° C., 100 mTorr). The resulting residue was further processed by a bleaching treatment at 90° C. for 2 hours. The refined product was stabilized by adding 500 ppm of α-tocopherol, and the final formulation was analyzed for fatty acid (gas chromatography with flame ionization detector, GC-FID) and lipid class compositions (high performance liquid chromatography-size exclusion chromatography-refractive index detector, HPLC-SEC-RI), respectively.

The final product composition was 96.5% DAG obtained in 49.6% yield with PV=0.1 and pAV=4.2. The amount of EPA in the DAG portion was 453 mg/g and the amount of DHA in the DAG portion was 370 mg/g.

Example 2

Preparation of eicosapentaenoic acid (EPA)/docosahexaenoic acid (DHA)-diacylglycerides (DAG)

The preparation of diacylglycerol from highly concentrated ethyl esters was facilitated by a one-pot hydrolysis followed by re-esterification in the presence of lipase B from *Candida antarctica* (CAL-B) under reduced pressure.

50 g of a mixture of omega-3 concentrated ethyl esters (EPA: 380 mg/g and DHA: 260 mg/g), glycerol (4.5 g), and CAL-B (0.5%, 0.25 mL-reaction A and 0.25%, 0.125 mL-reaction B) in water (10 mL) was added and stirred under vacuum (20 mTorr) at 65° C. After 2 hours and 4 hours, 5 mL water was added to each reaction. After 6 hours, 10 mL water was added to each reaction. The reaction was stirred overnight. After 24 hours, 10 mL water was added to each reaction and continued under vacuum. The reactions were stopped at 30 hours.

Upon completion, the oils were analyzed for lipid class compositions (LC-SEC-RI). Tables 4 and 5 show results of the lipid class composition.

TABLE 4

| Lipid class composition, Reaction A | | | |
|---|---|---|---|
| Time (hours) | TG (%) | DG (%) | MG (%) | FFA + EE (%) |
| 6 | 0.3 | 7.2 | 3.9 | 88.7 |
| 24 | 0 | 21.7 | 12.4 | 66 |
| 27 | 0 | 28.9 | 15 | 56 |
| 30 | 0 | 53.1 | 13.9 | 30 |

TABLE 5

| Lipid class composition, Reaction B | | | |
|---|---|---|---|
| Time (hours) | TG (%) | DG (%) | MG (%) | FFA + EE (%) |
| 6 | 0 | 18.3 | 8.2 | 73.6 |
| 24 | 0 | 31.9 | 16.3 | 51.8 |
| 27 | 0 | 36.3 | 18 | 45 |
| 30 | 0 | 44.7 | 17.3 | 37.9 |

In reaction A, after 24 hours, the amount of TG in the sample is 0%. In reaction B, no TGs were present in the starting oil. Short path distillation removes the unreacted ethyl ester, the generated monoacylglycerides, and other low boiling components, as shown in Example 1.

Example 3

Preparation of eicosapentaenoic acid (EPA)/docosahexaenoic acid (DHA)-diacylglycerides (DAG)

The preparation of diacylglycerol from highly concentrated ethyl esters was facilitated by a one-pot hydrolysis followed by re-esterification in the presence of lipase B from *Candida antarctica* (CAL-B) under reduced pressure.

200 g of a mixture of omega-3 concentrated ethyl esters (1:1 EPA:DHA), glycerol (14 g), and CAL-B (2 mL) in water (55 mL) was added and stirred under vacuum (20 mTorr) at 69° C. Water was added in amounts from 5-35 mL at hours 1-7. Upon completion, the oils were analyzed for lipid class compositions (LC-SEC-RI). Table 6 shows results of the lipid class composition.

TABLE 6

| Lipid class composition | | | | | |
|---|---|---|---|---|---|
| Time (hours) | TG (%) | DG (%) | MG (%) | FFA (%) | FFA + EE (%) | EE (%) |
| 0 | 0 | 0 | 0 | 0 | 100 | 100 |
| 4 | 0 | 30.8 | 12.9 | 21.9 | 56.3 | 34.5 |
| 7 | 0 | 49.3 | 5.1 | 20.7 | 45.6 | 24.9 |

The amount of TG in the sample is 0%. Short path distillation removes the unreacted ethyl ester, the generated monoacylglycerides, and other low boiling components, as shown in Example 1.

Example 4

Preparation of eicosapentaenoic acid (EPA)/docosahexaenoic acid (DHA)-diacylglycerides (DAG)

The preparation of diacylglycerol from highly concentrated ethyl esters was facilitated by a one-pot hydrolysis followed by re-esterification in the presence of lipase B from *Candida antarctica* (CAL-B) under reduced pressure.

200 g of a mixture of omega-3 concentrated ethyl esters (1:1 EPA:DHA), glycerol (16 g), and CAL-B (1 mL) in water (55 mL) was added and stirred under vacuum (20 mTorr) at 69° C. Water was added in amounts from 5-35 mL at hours 1-7. Upon completion, the oils were analyzed for lipid class compositions (LC-SEC-RI). Table 7 shows results of the lipid class composition.

TABLE 7

| Lipid class composition | | | | | |
|---|---|---|---|---|---|
| Time (hours) | TG (%) | DG (%) | MG (%) | FFA (%) | FFA + EE (%) | EE (%) |
| 0 | 0 | 0 | 0 | 0.2 | 100 | 99.8 |
| 4 | 0 | 28 | 15.2 | 24 | 56.8 | 32.8 |
| 7 | 0 | 44.7 | 10.5 | 21 | 44.8 | 23.9 |

The amount of TG in the sample is 0%. Short path distillation removes the unreacted ethyl ester, the generated monoacylglycerides, and other low boiling components, as shown in Example 1.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method for the production of one or more diglycerides comprising combining (i) an oil comprising at least one polyunsaturated fatty acid in the form of ethyl esters, free fatty acids, and/or combinations thereof, (ii) lipase, and (iii) glycerol in water, wherein water is added back into the reaction mixture one or more times during the reaction or continuously supplied during at least part of the reaction.

2. The method according to claim 1, wherein the lipase is derived from *Candida antarctica*.

3. The method according to claim 1 or 2, wherein the lipase is lipase B.

4. The method according to claim 1, wherein the ethyl esters comprise omega-3 ethyl esters.

5. The method according to claim 1, wherein the ethyl esters are eicosapentaenoic acid (EPA) ethyl ester, docosahexaenoic acid (DHA) ethyl ester, or a combination thereof.

6. The method according to claim 1, wherein the free fatty acids comprise omega-3 free fatty acids.

7. The method according to claim 1, wherein the free fatty acids are eicosapentaenoic acid (EPA), docosahexaenoic acid (DHA), or a combination thereof.

8. The method according to claim 1, wherein the combination of ethyl esters, free fatty acids, and/or combinations thereof, lipase, and glycerol in water is reacted for between about 2 hours to about 24 hours.

9. The method according to claim 1, wherein the reaction is performed under reduced pressure and sufficient temperature to evaporate ethanol and/or water from the reaction.

10. The method according to claim 1, wherein the temperature during the reaction is from about 30° C. to about 90° C.

11. The method according to claim 1, wherein the reaction mixture is washed one or more times.

12. The method according to claim 1, wherein the reaction mixture is dried after the reaction is complete.

13. The method according to claim 1, wherein any residual ethyl esters, monoacylglycerols, and/or free fatty acids are separated from the reaction mixture.

14. A method for the production of one or more diglycerides comprising:
   (a) combining (i) an oil comprising at least one polyunsaturated fatty acid in the form of ethyl esters, free fatty acids, and/or combinations thereof, (ii) lipase, and (iii) glycerol in water;
   (b) incubating the combination of (a) for about 2 to about 24 hours at about 30° C. to about 90° C. at reduced pressure to produce a reaction mixture, wherein water is added back into the reaction mixture one or more times during the reaction or continuously supplied during at least part of the reaction;
   (c) washing the reaction mixture obtained in (b);
   (d) drying the reaction mixture;
   (e) separating residual ethyl esters, monoacylglycerol(s), and/or free fatty acids from the reaction mixture.

15. The method of claim 14, wherein the lipase is lipase B from *Candida antarctica*.

16. A method for the production of diglycerides comprising combining (i) an oil comprising at least one polyunsaturated fatty acid in the form of ethyl esters, free fatty acid, and/or combinations thereof, (ii) lipase, and (iii) glycerol in water, wherein water is added back into the reaction or continuously supplied during at least part of the reaction to produce diglycerides with a high level of purity.

\* \* \* \* \*